United States Patent [19]

Krapcho et al.

[11] 4,166,907
[45] Sep. 4, 1979

[54] 3,3-DICHLORO-2-AZETIDINONE DERIVATIVES HAVING ANTIINFLAMMATORY ACTIVITY

[75] Inventors: John Krapcho, Somerset; Chester F. Turk, Kendall Park, both of N.J.

[73] Assignee: E. R. Squibb & Sons, Inc., Princeton, N.J.

[21] Appl. No.: 840,701

[22] Filed: Oct. 11, 1977

Related U.S. Application Data

[63] Continuation-in-part of Ser. No. 737,864, Nov. 1, 1976, Pat. No. 4,064,120.

[51] Int. Cl.$^2$ ............... C07D 413/12; C07D 401/12; C07D 403/12
[52] U.S. Cl. ..................... 544/111; 544/359; 260/239 A; 260/326.85; 260/326.37; 546/208; 546/232
[58] Field of Search ............... 544/111, 359; 260/293.69, 326.85

[56] References Cited

U.S. PATENT DOCUMENTS

| | | | |
|---|---|---|---|
| 3,194,801 | 7/1965 | Perelman | 260/239 A |
| 3,481,920 | 12/1969 | Hargrove | 260/239 A |

OTHER PUBLICATIONS

Duran et al., "Tetrahedron Letters," No. 3, 1970, pp. 245-248.
Sekiya et al., "Chemical & Pharmaceutical Bulletin," vol. 23, No. 10, 1975, pp. 2353-2357.
Morimoto et al., "Chemical Abstracts," vol. 84, 1976, col. 163799r.

*Primary Examiner*—Jose Tovar
*Assistant Examiner*—James H. Turnipseed
*Attorney, Agent, or Firm*—Lawrence S. Levinson; Donald J. Barrack

[57] ABSTRACT

Compounds having the formula

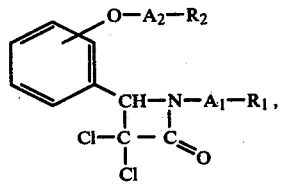

wherein $R_1$ is alkyl, cycloalkyl or aryl; $R_2$ is dialkylamino or a nitrogen containing heterocyclic group; $A_1$ is a saturated bond or an alkylene group having 1 to 4 carbon atoms; and $A_2$ is an alkylene group having 2 to 5 carbon atoms; have antiinflammatory activity.

6 Claims, No Drawings

3,3-DICHLORO-2-AZETIDINONE DERIVATIVES HAVING ANTIINFLAMMATORY ACTIVITY

This is a continuation-in-part of copending U.S. patent application Ser. No. 737,864, filed Nov. 1, 1976, now U.S. Pat. No. 4,064,120, issued Dec. 20, 1977.

BACKGROUND OF THE INVENTION

Sekiya and Morimoto, Chem. Pharm. Bull., 23, 2353 (1975), disclose that the reaction of trichloroacetic anhydride with Schiff bases yields 3,3-dichloro-2-azetidinones. Exemplary compounds are disclosed, but there is no discussion of any utility for the compounds prepared. Unlike the compounds of Sekiya et al., the compounds of the instant invention contain a basic group making possible the preparation of water-soluble acid-addition salts.

BRIEF DESCRIPTION OF THE INVENTION

Compounds having the formula

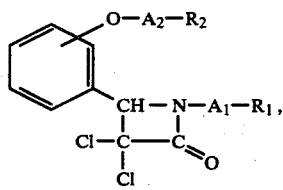

or a pharmaceutically acceptable salt thereof, have useful antiinflammatory activity. In formula I, and throughout the specification, the symbols are as defined below.

$R_1$ can be alkyl, cycloalkyl or aryl;

$R_2$ can be dialkylamino or a nitrogen containing heterocyclic group selected from 1-pyrrolidinyl, 1-piperidinyl, 4-morpholinyl, 1-piperazinyl, and 4-alkyl-1-piperazinyl;

$A_1$ can be a saturated bond or an alkylene group having 1 to 4 carbon atoms; and $A_2$ can be an alkylene group having 2 to 5 carbon atoms.

The term "aryl," as used throughout the specification, whether by itself or as part of a larger group, refers to phenyl or phenyl substituted with a halogen, alkyl, alkoxy, trifluoromethyl, or nitro group.

The terms "alkyl" and "alkoxy," as used throughout the specification, whether by themselves or as part of larger groups, refer to groups having 1 to 6 carbon atoms.

The term "halogen," as used throughout the specification, refers to fluorine, chlorine, bromine or iodine; chlorine and bromine are preferred.

The term "cycloalkyl," as used throughout the specification, refers to groups having 3 to 7 carbon atoms.

The term "alkylene," as used throughout the specification, refers to a straight or branched chain, divalent, saturated hydrocarbon group.

DETAILED DESCRIPTION OF THE INVENTION

The compounds of this invention can be prepared using as starting materials a benzaldehyde having the formula

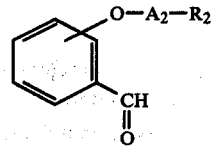

and a primary amine having the formula $$H_2N-A_1-R_1 \qquad \text{III}$$

Reaction of a benzaldehyde of formula II with an amine of formula III yields the corresponding Schiff base having the formula

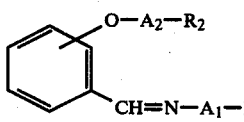

The reaction can be run in an organic solvent, e.g., an aromatic hydrocarbon such as toluene, and will preferably be run at the reflux temperature of the solvent.

Reaction of a Schiff base of formula IV with trichloroacetic anhydride, in accordance with the procedure set forth by Sekiya and Morimoto, Chem. Pharm. Bull., 23, 2353 (1975), yields the corresponding 3,3-dichloro-2-azetidinone of formula I.

The pharmaceutically acceptable salts of the compounds of formula I are readily prepared using procedures well known in the art. Acid-addition salts are specifically contemplated. Exemplary salts are the hydrohalides, sulfate, nitrate, phosphate, oxalate, tartrate, maleate, citrate, benzenesulfonate, and others.

The compounds of formula I, and the pharmaceutically acceptable salts thereof, can be used for the treatment of inflammation in mammalian species such as mice, dogs, cats, monkeys, etc. Joint tenderness and stiffness (in conditions such as rheumatoid arthritis) are relieved by the compounds of this invention. Formulation of the compounds can be carried out according to accepted pharmaceutical practice in oral dosage forms such as tablets, capsules, elixirs or powders, or in injectable form in a sterile vehicle. The compounds of this invention can be administered in amounts of about 0.1 to 2.0 grams per 70 kilograms of animal body weight per day, preferably about 0.1 to 1.0 grams per 70 kilograms of animal body weight per day.

The following examples are specific embodiments of this invention.

EXAMPLE 1

3,3-Dichloro-4-[2-[3-(dimethylamino)propoxy]phenyl]-1-(2-phenylethyl)-2-azetidinone, hydrochloride (1:1)

(A)

N-[[2-[3-(Dimethylamino)propoxy]phenyl]methylene]-benzeneethanamine

A solution of 32.5 g of 2-(3-dimethylaminopropoxy)-benzaldehyde and 18.9 g of phenethylamine in 150 ml of toluene is heated at reflux for one hour. After 30 minutes, one mole equivalent of water is collected in a Dean-Stark trap. After cooling to approximately 50° C., the solvent is removed using a rotary evaporator and the oily residue is distilled to give 36.2 g of the title compound, boiling point 165°–167° C. at 0.05 mm of Hg.

(B)

3,3-Dichloro-4-[2-[3-(dimethylamino)propoxy]phenyl]-1-(2-phenylethyl)-2-azetidinone, hydrochloride (1:1)

A solution of 13.5 g of N-[[2-[3-(dimethylamino)propoxy]phenyl]methylene]benzeneethanamine in 50 ml of xylene is stirred, cooled to 18° C. and treated with a solution of 18.0 g of trichloroacetic anhydride in 30 ml of xylene while maintaining the temperature at 15°–20° C. The solution is slowly heated to 100° C.—a vigorous evolution of carbon dioxide takes place at this point. After heating at 120°–130° C. for 30 minutes, the solution is cooled and poured onto 300 ml of ice-water. The mixture is treated with 20 g of potassium carbonate and extracted with 200 ml of ether. The gummy ether-insoluble material and aqueous phase is discarded and the ether phase is extracted with a solution of 5 ml of concentrated hydrochloric acid in 100 ml of water. This aqueous layer is treated with 6 g of potassium carbonate and the liberated base is extracted with 100 ml and 50 ml portions of ether. The ether phases are combined, dried, treated with Darco and filtered. Evaporation of the filtrate gives 11.6 g of syrup. The latter is dissolved in 50 ml of methanol and treated with a solution of 4.4 g of fumaric acid in 100 ml of methanol. The solution is concentrated on a rotary evaporator and the residual semi-solid (17.9 g) is crystallized from 100 ml of acetonitrile to give 12.8 g of salt, melting point 139°–141° C. After recrystallization from 140 ml of acetonitrile, the solid weighs 12.0 g, melting point 139°–141° C. This material is pulverized, suspended in 200 ml of water and treated with a solution of 15 g of potassium carbonate. The liberated base is extracted with a 200 ml and a 50 ml portion of ether. The ether phases are combined, dried, filtered, and the solvent evaporated on a rotary evaporator to give 8.3 g of base. The latter is dissolved in 100 ml of acetonitrile and treated with a slight excess of 6.1 N alcoholic hydrogen chloride. The product slowly crystallizes. After standing for about 16 hours in a cold room, the solid weighs 6.5 g, melting point 196°–198° C. Evaporation of the filtrate to about 30 ml gives an additional 1.5 g of product, melting point 196°–198° C. Recrystallization of the 6.5 g of material from 70 ml of acetonitrile gives 5.6 g of solid, melting point 196°–198° C.

EXAMPLE 2

3,3-Dichloro-4-[2-[3-(dimethylamino)propoxy]phenyl]-1-(phenylmethyl)-2-azetidinone, oxalate salt (1:1)

(A)

N-[[2-[3-(Dimethylamino)propoxy]phenyl]methylene]benzylamine

Following the procedure of Example 1, part A, but substituting benzylamine for phenethylamine, yields the title compound, boiling point 175°–178° C. at 0.05 mm of Hg.

(B)

3,3-Dichloro-4-[2-[3-(dimethylamino)propoxy]phenyl]-1-(phenylmethyl)-2-azetidinone, oxalate salt (1:1)

A stirred solution of 17.1 g of N-[[2-[3-(dimethylamino)propoxy]phenyl]methylene]benzylamine in 50 ml of xylene is cooled to 10° C. and treated with a solution of 22.0 g of trichloroacetic anhydride in 30 ml of xylene while maintaining the temperature below 20° C. The solution is slowly heated to 90° C. (evolution of carbon dioxide begins at this point) and maintained at 110°–120° C. for 15 minutes. The solution is cooled and poured into 300 ml of ice water and the free base is isolated in the manner described in Example 1 to give 16.9 g of residue. Part of the base (15.2 g) is treated with 300 ml of ether and filtered. The filtrate is concentrated to give 14.2 g of base. The base is dissolved in 40 ml of methanol, treated with a solution of 4.0 g of fumaric acid in 100 ml of methanol and the resulting solution is concentrated to give 22.1 g of syrup. This residue is treated with 300 ml of ether to give 16.4 g of solid. This material is pulverized in a mortar, suspended in 250 ml of ether and filtered to give 16.2 g of solid, melting point 94°–101° C. Part of this salt (15.8 g) is crystallized from 50 ml of acetonitrile to give 12.6 g of solid, melting point 101°–103° C. After recrystallization from 30 ml of acetonitrile, the material weighs 11.4 g, melting point 103°–105° C. Since this salt does not give a satisfactory Cl analysis (about 1.5% low), 9.75 g of material is converted to the free base (potassium carbonate extraction) weighing 4.95 g. The hydrochloride salt of this base is a low-melting hygroscopic solid. The base is dissolved in 25 ml of acetonitrile, treated with a solution of 1.1 g of oxalic acid in 25 ml of acetonitrile and the resulting solution is slowly diluted to 250 ml with ether, yielding 5.4 g of solid, melting point 128°–130° C. After recrystallization from 43 ml of isopropanol, the oxalate weighs 5.4 g, melting point 132°–134° C. Since the chlorine value on this material is about 1% low, it is pulverized and suspended in 10 ml of water for 1 hour, cooled, filtered, washed with cold water and dried in a desiccator. This solid (4.4 g, melting point 135°–137° C.) is dissolved in 15 ml of warm acetonitrile, cooled and gradually diluted to 100 ml with ether to give 4.3 g of the title compound, melting point 135°–137° C.

EXAMPLE 3

1-Butyl-3,3-dichloro-4-[2-[3-(dimethylamino)propoxy]phenyl]-2-azetidinone, hydrochloride (1:1)

(A)

N-[[2-[3-(dimethylamino)propoxy]phenyl]methylene]butanamine

Following the procedure of Example 1, part A, but substituting n-butylamine for phenethylamine, yields the title compound, boiling point 124°–128° C. at 0.1–0.2 mm of Hg.

(B)

1-Butyl-3,3-dichloro-4-[2-[3-(dimethylamino)propoxy]phenyl]-2-azetidinone, hydrochloride (1:1)

Ten grams of N-[[2-[3-(dimethylamino)propoxy]phenyl]methylene]butanamine and 15.9 g of trichloroacetic anhydride are reacted in 80 ml of xylene as described in Example 1, part B, (maintained at 110°–120° C. for 30 minutes) yielding 10.9 g of crude base, which in turn yields 10.8 g of fumarate salt, melting point 142°–144° C. Crystallization from 40 ml of acetonitrile gives 10.2 g of solid, melting point 143°–145° C. The fumarate salt is converted to the free base, 7.6 g of which is dissolved in 100 ml of ether and treated with 50 ml of ether containing 4.0 ml of 5.1 N alcoholic hydrogen chloride. The hydrochloride salt separates as an oil, which crystallizes on seeding, rubbing, and cooling for about 16 hours. Crystallization from 90 ml of ethyl acetate yields 7.3 g of the title compound, melting point 119°–121° C. (sintering at 114° C.).

EXAMPLE 4

3,3-Dichloro-4-[4-[3-(dimethylamino)propoxy]phenyl]-1-(2-phenylethyl)-2-azetidinone, hydrochloride (1:1)

(A)

N-[[4-[3-(dimethylamino)propoxy]phenyl]methylene]-benzeneethanamine

Following the procedure of Example 1, part A, but substituting 4-(3-dimethylaminopropoxy)benzaldehyde for 2-(3-dimethylaminopropoxy)benzaldehyde, yields the title compound, boiling point 184°–189° C. at 0.1–0.2 mm of Hg.

(B)

3,3-Dichloro-4-[4-[3-(dimethylamino)propoxy]phenyl]-1-(2-phenylethyl)-2-azetidinone, hydrochloride (1:1)

Ten grams of N-[[4-[3-(dimethylamino)propoxy]phenyl]methylene]benzeneethanamine and 13.3 g of trichloroacetic anhydride are reacted in 65 ml of xylene as described in Example 1, part B, (maintained at 110°–120° C. for 30 minutes) yielding 11.4 g of crude base, which in turn yields 7.0 g of fumarate salt, melting point 162°–164° C. Recrystallization from a warm mixture of 35 ml of ethanol and 35 ml of ether gives 6.0 g of solid, melting point 167°–169° C. The fumarate salt is converted to the free base, 4.3 g of which is dissolved in 25 ml of warm acetonitrile, cooled, treated with 1.7 ml of 6.1 N alcoholic hydrogen chloride, and diluted with 50 ml of ether. On seeding, rubbing and cooling for about 16 hours, 3.5 g of the hydrochloride salt is obtained, melting point 148°–150° C. (sintering at 140° C.). Recrystallization from a warm mixture of 15 ml of acetonitrile and 30 ml of ether yields 3.1 g of the title compound, melting point 150°–152° C. (sintering at 140° C.).

EXAMPLE 5

3,3-Dichloro-4-[2-[3-(dimethylamino)propoxy]phenyl]-1-phenyl-2-azetidinone, hydrochloride (1:1)

(A)

N,N-Dimethyl-3-[2-[(phenylimino)methyl]phenoxy]-propanamine

A solution of 15 g of 2-(3-dimethylaminopropoxy)benzaldehyde and 8.0 g of aniline (distilled over zinc dust) in 300 ml of ethanol is kept at room temperature for 22 hours, refluxed for 2 hours, and the solvent removed on a rotary evaporator. The residue (21.3 g) is distilled to give 17 g of an oil; boiling point 171°–175° C./0.2 mm of Hg.

(B)

3,3-Dichloro-4-[2-[3-(dimethylamino)propoxy]phenyl]-1-phenyl-2-azetidinone, hydrochloride (1:1)

Ten grams of material from part A and 14.6 g of trichloroacetic anhydride are reacted in 80 ml of xylene as described under Example 1 to give 10.4 g of crude base as an oil. The oil (9.7 g) is dissolved in dichloromethane, treated with 1 equivalent of alcoholic hydrogen chloride, and the solvents evaporated to give a glass-like residue (11.8 g), which is dissolved in 50 ml of acetonitrile and diluted with 120 ml of ether. On seeding and rubbing, the crystalline hydrochloride salt gradually separates; crude yield, after cooling for about 16 hours, 5.8 g, melting point 157°–160° C. (sintering at 145° C.). Following crystallization from 25 ml of acetonitrile, the solid weighs 4.0 g; melting point 159°–161° C. (sintering at 147° C.).

EXAMPLES 6–22

Following the procedure of Example 1, but substituting the compound listed in column 1 for 2-(3-dimethylaminopropoxy)benzaldehyde and the compound listed in column II for phenethylamine, and omitting the final salt formation, yields the compound listed in column III.

| Column I | Column II | Column III |
| --- | --- | --- |
| 2-(2-diisopropylaminoethoxy)-benzaldehyde | isopropylamine | 3,3-dichloro-4-[2-[2-(diisopropylamino)-ethoxy]phenyl]-1-isopropyl-2-azetidinone |
| 3-[4-(1-pyrrolidinyl)butoxy]-benzaldehyde | n-pentylamine | 3,3-dichloro-1-pentyl-4-[3-[4-(1-pyrrolidinyl)butoxy]phenyl]-2-azetidinone |
| 4-[2-(1-piperidinyl)ethoxy]-benzaldehyde | isopropylamine | 3,3-dichloro-1-isopropyl-4-[4-[2-(1-piperidinyl)ethoxy]phenyl]-2-azetidinone |
| 2-[5-(4-morpholinyl)pentoxy]-benzaldehyde | phenethylamine | 3,3-dichloro-4-[2-[5-(4-morpholinyl)-pentoxy]phenyl]-1-(2-phenylethyl)-2-azetidinone |
| 3-[2-(1-piperazinyl)ethoxy]-benzaldehyde | phenethylamine | 3,3-dichloro-1-(2-phenylethyl)-4-[3-[2-(1-piperazinyl)ethoxy]phenyl]-2-azetidinone |
| 4-[3-(4-methyl-1-piperazinyl)-propoxy]benzaldehyde | phenethylamine | 3,3-dichloro-4-[4-[3-(4-methyl-1-piperazinyl)propoxy]phenyl]-1-(2-phenylethyl)-2-azetidinone |
| 3-(2-dimethylaminoethoxy)-benzaldehyde | cyclopropylamine | 3,3-dichloro-1-cyclopropyl-4-[3-[2-(dimethylamino)ethoxy]phenyl]-2-azetidinone |
| 3-(3-dimethylamino-2-methyl-propoxy)benzaldehyde | cycloheptylmethyl-amine | 3,3-dichloro-1-(cycloheptylmethyl)-4-[3-[3-(dimethylamino-2-methyl)propoxy]phenyl-2-azetidinone |
| 3-[2-(1-pyrrolidinyl)ethoxy]-benzaldehyde | 4-chloroaniline | 3,3-dichloro-1-(4-chlorophenyl)-4-[3-[2-(1-pyrrolidinyl)ethoxy]phenyl]-2-azetidinone |
| 2-[3-(1-piperidinyl)propoxy]-benzaldehyde | 3-trifluoromethyl-aniline | 3,3-dichloro-4-[2-[3-(1-piperidinyl)propoxy]-phenyl]-1-(3-trifluoromethylphenyl)-2-azetidinone |
| 2-[4-(4-morpholinyl)butoxy]-benzaldehyde | o-toluidine | 3,3-dichloro-1-(2-methylphenyl)-4-[2-[4-(4-morpholinyl)butoxy]phenyl]-2-azetidinone |
| 3-[3-(1-piperazinyl)propoxy]-benzaldehyde | 4-nitroaniline | 3,3-dichloro-1-(4-nitrophenyl)-4-[3-[3-(1-piperazinyl)propoxy]phenyl]-2-azetidinone |
| 2-(2-dimethylaminoethoxy)- | 2-methoxybenzyl- | 3,3-dichloro-4-[2-[2-(dimethylamino)ethoxy]- |

| Column I | Column II | Column III |
|---|---|---|
| benzaldehyde | amine | phenyl]-1-(2-methoxybenzyl)-2-azetidinone |
| 3-(3-methylethylaminopropoxy)-benzaldehyde | t-butylamine | 1-(t-butyl)-3,3-dichloro-4-[3-[3-(methylethyl-amino)propoxy]phenyl]-2-azetidinone |
| 2-(3-methylethylaminopropoxy)-benzaldehyde | 3-phenylpropyl-amine | 3,3-dichloro-4-[2-[3-(methylethylamino)propoxy]-phenyl]-1-(3-phenylpropyl)-2-azetidinone |
| 2-(3-methylethylaminopropoxy)-benzaldehyde | 4-phenylbutylamine | 3,3-dichloro-4-[2-[3-(methylethylamino)propoxy]-phenyl]-1-(4-phenylbutyl)-2-azetidinone |
| 2-(3-dimethylaminopropoxy)-benzaldehyde | cyclohexylamine | 3,3-dichloro-1-cyclohexyl-4-[2-[3-(dimethylamino)-propoxy]phenyl]-2-azetidinone |

EXAMPLE 23

3,3-Dichloro-4-[2-[3-(4-morpholinyl)propoxy]phenyl]-1-(2-phenylethyl)-2-azetidinone, hydrochloride salt (1:1)

A. 2-[3-(4-Morpholinyl)propoxy]benzaldehyde

Salicylaldehyde (17 g) is treated first with 6.7 g of 50% sodium hydride in 110 ml of dimethylformamide and then with 92 ml of a 2 N toluene solution of N-(3-chloropropyl)morpholine. The mixture is heated at 105°–110° C. for 4 hours, cooled and poured into 300 ml of water. The product is extracted three times with ether. The extracts are combined, dried, concentrated on a rotary evaporator and the residue distilled to give 32.3 g of product as an oil, boiling point 155°–160° C. at 0.1–0.2 mm of Hg.

B. N-[[2-[3-(4-Morpholinyl)propoxy]phenyl]methylene]-benzeneethanamine

2-[3-(4-Morpholinyl)propoxy]benzaldehyde (31.7 g) is reacted with 15.8 g of phenethylamine in 130 ml of toluene following the procedure described in Example 1A to yield 34.3 g of product as an oil, boiling point 215°–219° C. at 0.2–0.3 mm of Hg.

C. 3,3-Dichloro-4-[2-[3-(4-morpholinyl)propoxy]phenyl]-1-(2-phenylethyl)-2-azetidinone, hydrochloride salt (1:1)

N-[[2-[3-(4-morpholinyl)propoxy]phenyl]methylene]benzeneethanamine (16.9 g) and 20 g of trichloroacetic anhydride are reacted as described in Example 1B (heated 30 minutes at 120°–128° C.) yielding 20.1 g of crude base as an oil. Crystallization of this material from 100 ml of isopropyl ether yields 14 g of the free base of the title compound, melting point 80°–82° C. (sintering at 75° C.).

The free base (13.8 g) is suspended in 70 ml of 95% ethanol, stirred, cooled, treated with 5.5 ml of 5.5 N ethanolic hydrogen chloride and diluted to 500 ml with ether. On seeding and rubbing, 13 g of the crystalline hydrogen chloride salt separates, melting point 172°–174° C. (sintering at 157° C.). Following crystallization from 65 ml of acetonitrile the solid weighs 10.2 g, melting point 172°–174° C.

What is claimed is:

1. A compound having the formula

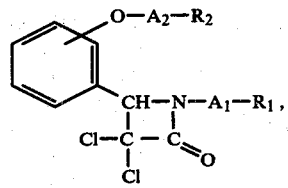

or a pharmaceutically acceptable salt thereof, wherein $R_1$ is alkyl, cycloalkyl, phenyl, or phenyl substituted with a halogen, alkyl, alkoxy, trifluoromethyl, or nitro group; $R_2$ is 1-pyrrolidinyl, 1-piperidinyl, 4-morpholinyl, 1-piperazinyl or 4-alkyl-1-piperazinyl; $A_1$ is a saturated bond or an alkylene group having 1 to 4 carbon atoms; $A_2$ is an alkylene group having 2 to 5 carbon atoms; wherein alkyl and alkoxy are groups having 1 to 6 carbon atoms; and cycloalkyl is a group having 3 to 7 carbon atoms.

2. A compound in accordance with claim 1 wherein $R_1$ is alkyl.

3. A compound in accordance with claim 1 wherein $R_1$ is phenyl or phenyl substituted with a halogen, alkyl, alkoxy, trifluoromethyl or nitro group.

4. A compound in accordance with claim 3 wherein $R_1$ is phenyl.

5. A compound in accordance with claim 1 wherein $R_2$ is 4-morpholinyl.

6. The compound in accordance with claim 5 having the name 3,3-dichloro-4-[2-[3-(4-morpholinyl)propoxy]-phenyl]-1-(2-phenylethyl)-2-azetidinone, hydrochloride salt (1:1).